United States Patent
Kopperschmidt et al.

(10) Patent No.: US 9,724,455 B2
(45) Date of Patent: Aug. 8, 2017

(54) DIALYSATE FLOW CONTROL

(75) Inventors: Pascal Kopperschmidt, Dittelbrunn (DE); Alfred Gagel, Litzendorf (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 571 days.

(21) Appl. No.: 13/599,028

(22) Filed: Aug. 30, 2012

(65) Prior Publication Data

US 2013/0056418 A1    Mar. 7, 2013

Related U.S. Application Data

(60) Provisional application No. 61/529,965, filed on Sep. 1, 2011.

(30) Foreign Application Priority Data

Sep. 1, 2011   (DE) .......................... 10 2011 053 200

(51) Int. Cl.
  *A61M 1/14*   (2006.01)
  *A61M 1/16*   (2006.01)
  *A61M 1/36*   (2006.01)

(52) U.S. Cl.
  CPC ............ *A61M 1/16* (2013.01); *A61M 1/1605* (2014.02); *A61M 1/36* (2013.01); *A61M 1/3609* (2014.02); *A61M 2205/3317* (2013.01); *A61M 2205/3368* (2013.01)

(58) Field of Classification Search
  CPC .................................................. A61M 1/1605
  See application file for complete search history.

(56) References Cited

U.S. PATENT DOCUMENTS

| | | | |
|---|---|---|---|
| 5,100,554 A | | 3/1992 | Polaschegg |
| 5,110,477 A | | 5/1992 | Howard et al. |
| 5,595,182 A | * | 1/1997 | Krivitski ............. A61B 5/0275 600/454 |
| 6,156,002 A | | 12/2000 | Polaschegg et al. |
| 6,187,199 B1 | | 2/2001 | Goldau |
| 6,648,845 B1 | * | 11/2003 | Gotch .................... A61M 1/16 210/646 |
| 6,691,040 B2 | | 2/2004 | Bosetto et al. |
| 7,815,809 B2 | | 10/2010 | Jansson et al. |

(Continued)

FOREIGN PATENT DOCUMENTS

| | | |
|---|---|---|
| CN | 101098721 | 1/2008 |
| CN | 101466419 | 6/2009 |

(Continued)

*Primary Examiner* — Krishnan S Menon
*Assistant Examiner* — Bradley R Spies
(74) *Attorney, Agent, or Firm* — Jacobson Holman, PLLC.

(57) ABSTRACT

Method and apparatus for controlling the dialysate flow in a dialysis device. A change of the value of a control factor, caused by a variation of a property of the dialysate or of the blood or by a change of the dialysate flow, is determined in order to control the dialysate flow. The control factor is a measure for the exchange of substances via the dialyzer and thus the effectiveness of the dialyzer. If the change of the value of the control factor exceeds a limit, the dialysate flow is increased. On the other hand, the dialysate flow is reduced if the change of the value of the control factor falls short of the limit range.

8 Claims, 1 Drawing Sheet

(56) References Cited

U.S. PATENT DOCUMENTS

| | | | |
|---|---|---|---|
| 2005/0148923 A1* | 7/2005 | Sternby | A61B 5/0275 604/4.01 |
| 2005/0251086 A1* | 11/2005 | Sternby | A61M 1/342 604/4.01 |
| 2008/0097272 A1 | 4/2008 | Daniel et al. | |
| 2009/0221948 A1* | 9/2009 | Szamosfalvi | A61M 1/3672 604/6.07 |
| 2010/0042035 A1 | 2/2010 | Moissl et al. | |
| 2010/0168925 A1 | 7/2010 | Hilgers et al. | |
| 2012/0029937 A1* | 2/2012 | Neftel et al. | 705/2 |

FOREIGN PATENT DOCUMENTS

| | | | |
|---|---|---|---|
| CN | 101516416 | 8/2009 | |
| DE | 197 39 100 | 2/1999 | |
| DE | 10 2005 001051 | 7/2006 | |
| DE | 10 2006 045437 | 4/2008 | |
| EP | 0 911 043 | 4/1999 | |
| JP | H03173569 | 7/1991 | |
| JP | 2001029456 | 2/2001 | |
| JP | 2001504735 | 4/2001 | |
| JP | 2001218837 | 8/2001 | |
| JP | 2001511029 | 8/2001 | |
| JP | 2005537840 | 12/2005 | |
| JP | 2009539440 | 11/2009 | |
| JP | 2010-504181 | 2/2010 | |
| WO | WO 98/32476 | 7/1998 | |
| WO | WO 2005/107833 | 11/2005 | |
| WO | WO 2007/140993 | 12/2007 | |
| WO | WO 2010/108955 | 9/2010 | |
| WO | WO 2010108955 A1 * | 9/2010 | A61M 1/16 |
| WO | WO 2011074603 | 6/2011 | |

\* cited by examiner

DIALYSATE FLOW CONTROL

This is a complete application claiming benefit of provisional 61/529,965, filed Sep. 1, 2011, which has a priority of German no. 10 2011 053 200.5 filed Sep. 1, 2011, hereby incorporated by reference.

TECHNICAL FIELD

The invention relates to a method and an apparatus for controlling the dialysate flow in a dialysis device.

BACKGROUND ART

According to the meaning of the terms used herein, dialysis devices are in particular devices for the extracorporeal blood treatment, which for example can be configured for haemodialysis and/or ultrafiltration.

During haemodialysis, the blood of a patient in a dialysis device is led in an extracorporeal blood cycle through a blood chamber of a dialyzer. The blood chamber is separated by a semipermeable membrane from the dialysis chamber of the dialyser. The dialysis chamber is perfused by a dialysate. The dialysate contains blood electrolytes in a concentration that corresponds to the concentration in the blood of a healthy individual. During the treatment, the blood and the dialysate are led past opposite sides of the semipermeable membrane in general in a counterflow with a predetermined flow rate. The substances, which should be excreted by urine diffuse through the membrane from the blood chamber into the dialysis chamber, while at the same time electrolytes that are present in the blood and in the dialysate diffuse from the chamber of higher concentration to the chamber of lower concentration.

Additionally the blood can be dehydrated by building up a pressure gradient on the semipermeable membrane of the dialyser, and as a consequence water is pressed out of the blood to the side of the dialysate chamber. This process is called ultarfiltration.

The effectiveness of the dialyser in the dialysis device and, thus, in the blood treatment inter alia also depends on the size of the dialysate flow, i.e. the flow rate of the dialysate. A high dialysate flow can increase the effectiveness of the blood treatment up to an upper limit, however, also leads to an increase of the consumption of dialysate and energy.

Accordingly, it is desirable and thus an object of the invention to determine the amount of dialysate flow in a dialysate device such that the effectiveness of the blood treatment is as high as possible and at the same time the consumption of dialysate and energy is kept in an acceptable range. Thereby it is further desirable that such a definition of the amount of dialysate flow can be carried out independently of the knowledge of the used dialyser type, the blood flow or specific patient parameters, as for example the presence of a recirculation.

SUMMARY OF THE INVENTION

This object is solved by the method and the apparatus according to the independent claims. Advantageous embodiments of the method and the apparatus can be taken from the respective dependent claims.

According to the present invention in a method for controlling the dialysate flow a blood chamber of a dialyser is perfused with blood and a dialysate chamber separated from the blood chamber by a semipermeable membrane is perfused with a dialysate. A change of the value of a control factor, caused by a variation of a property of the dialysate or of the blood or by a change of the dialysate flow, is determined in order to control the dialysate flow. The control factor is a measure for the exchange of substances via the dialyser and thus the effectiveness of the dialyser. If the change of the value of the control factor exceeds a limit, the dialysate flow is increased. On the other hand, the dialysate flow is reduced, if the change of the value of the control factor falls short of the limit.

According to the invention an apparatus for controlling a dialysate flow comprises: a dialyzer with a blood chamber to be perfused with blood and with a dialysate chamber separated from the blood chamber by a semipermeable membrane, which is to be perfused with a dialysate, means to generate the dialysate flow through the dialysate chamber, a unit for determining a control factor, which is a measure for the exchange of substances via the dialyser and thus the effectiveness of the dialyser, and a control facility for controlling the dialysate flow through the dialysate chamber of the dialyzer, if a change of the value of a control factor, caused by a variation of a property of the dialysate or of the blood or by a change of the dialysate flow, does not lie within a limit, wherein the control facility instructs the means for generating the dialysate flow to increase the dialysate flow, if the change of the value of the control factor exceeds the limit, and to reduce the dialysate flow, if the change of the value of the control factor falls short of the limit.

If the change of the value of the control factor is caused by a change of the dialysate flow, the control factor preferably has a ratio or a difference out of values to be assigned after and before the change of the dialysate flow, wherein the values are of a property of the dialysate or of the blood after the dialyzer. I.e. for determining the ratio or the difference, the value of a property of the dialysate or of the blood at the outlet of the dialyzer, wherein the change of the dialysate flow has already taken place when the dialysate or blood enters into the dialyzer, and the value of dialysate or blood, wherein the change of the dialysate flow has not yet taken place when the dialysate or blood enters into the dialyzer, are used.

If the change of the value of the control factor is caused by a variation of a property of the dialysate or the blood, the control factor preferably has a ratio or a difference out of values of the property after and before the dialyzer. I.e. in terms of a variation of a property of the dialysate the ratio or the difference can be determined on the one hand by the value of the property of the dialysate after the dialyzer or the value of the property of the blood after the dialyzer, and on the other hand by the value of the property of the dialysate before the dialyzer or the value of the property of the blood before the dialyzer. Accordingly, in terms of a variation of a property of the blood it applies that the ratio or the difference can be determined as well on the one hand by the value of the property of the dialysate after the dialyzer or the value of the property of the blood after the dialyzer, and on the other hand by the value of the property of the dialysate before the dialyzer or the value of the property of the blood before the dialyzer. The control factor preferably has the ratio of the value of a property of the dialysate after the dialyzer to the value of the property of the dialysate before the dialyzer. A difference, contained in the expression of the control factor, is preferably generated out of the value of a property of the dialysate after the dialyzer and the value of the property of the dialysate before the dialyzer.

The property of the dialysate preferably is the electrical conductivity or the temperature of the dialysate, and the property of the blood preferably is the electrical conductivity or the temperature of the blood.

In order to determine the change of the value of the control factor, the property of the dialysate or of the blood preferably is varied continuously at least for a time sequence. The change of the value of the control factor itself is determined preferably by a derivation of the control factor from to the dialysate flow.

The limits correspond preferably to a range of tolerance about the value of 10, 11, 12, 13, 14, 15, 16, 17, 18, 19 or 20 percent of the value of the control factor per change of the dialysate flow of 100 ml/min. Thereby the range of tolerance preferably comes to one percent of the value of the control factor per change of the dialysate flow of 100 ml/min, so that in terms of a value of 10 percent of the value of the control factor per change of the dialysate flow of 100 ml/min the limit ranges from 9.5 to 10.5 percent of the value of the control factor per change of the dialysate flow of 100 ml/min is sufficient. Alternatively the range of tolerance also can be zero, so that the limit coincides with a limit value as for example 10, 11, 12, 13, 14, 15, 16, 17, 18, 19 or 20 percent of the value of the control factor per change of the dialysate flow of 100 ml/min.

An apparatus for controlling the dialysate flow according to the invention preferably is employed in an apparatus for extracorporeal blood treatment as for example a dialysate device.

In the following, the invention is described in more detail in association with the drawings.

BRIEF DESCRIPTION OF THE DRAWINGS

It shows.

DESCRIPTION OF THE EMBODIMENTS

Figure 1:
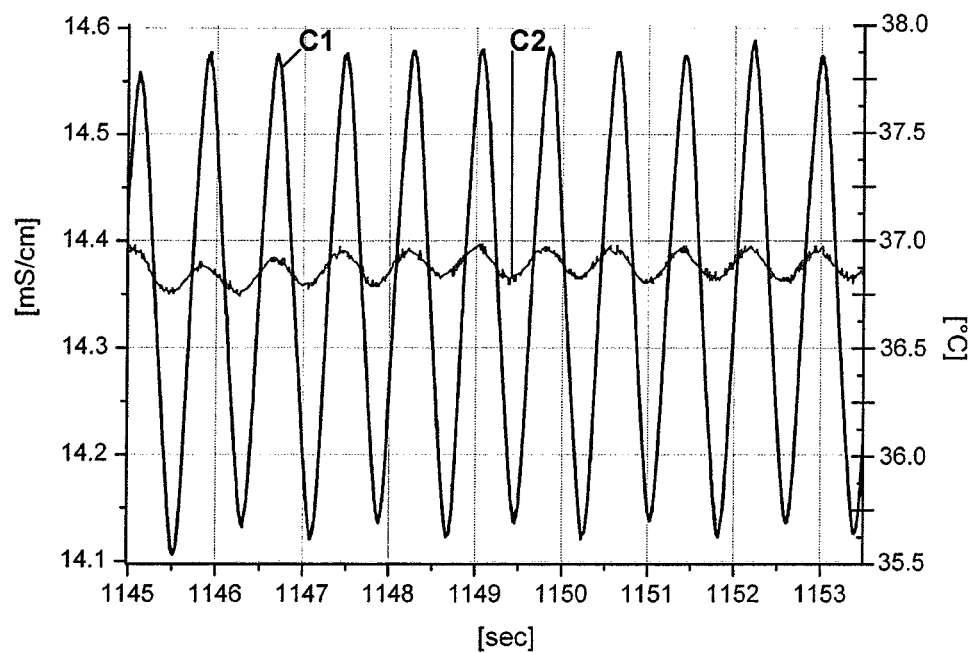
FIG. 1 the chronological sequences of the electrical conductivity (left vertical axis) and of the temperature (right vertical axis) of the dialysate before (graph C1) and after (graph C2) the dialyzer in terms of a variation of the concentrate injection or in terms of a variation of the heating of the dialysate and a dialysate flow of 800 ml/min, FIG. 2 the amplitude ratio of the values of the electrical conductivity or of the temperature of the dialysate before and after the dialyzer as function of the dialysate flow (graph C3 with left vertical axis) as well as the relative change of the amplitude ratio as function of the dialysate flow (graph C4 with right vertical axis).

The control factor $$k_d = Q_d * (A_{d,out}(Q_d) - A_{d,out}(0))/A_{d,in}$$

can serve as a measure for the effectiveness of a dialyzer. Thereby $Q_d$ describes the dialysate flow in the dialyzer, while $A_{d,in}$ and $A_{d,out}$ describe a property of the dialysate, as for example the electrical conductivity or the temperature of the dialysate, before or after the dialyzer. $A_{d,out}(0)$ indicates the value of the property of the dialysate in terms of a missing cleaning performance, for example in terms of missing blood flow. In terms of a rising dialysate flow the control factor $k_d$ increases, in case a cleaning performance exists. However, the gain of the control factor $k_d$ decreases constantly. I.e. in terms of a further increase of the effectiveness of the dialyzer the consumption of dialysate and energy rises quickly due to an increase of the dialysate flow, so that from a certain limit a further increase of the dialysate flow in order to increase the effectiveness of the dialyzer is not sensible anymore.

The derivation of the control factor $k_d$ divided by the dialysate flow $Q_d$ over the dialysate flow $Q_d$, specifies the change of the control factor $k_d/Q_d$ and thus specifies the normalised gain of the effectiveness of the dialyzer due to a change of the dialysate flow $Q_d$.

$$\epsilon = \delta(k_d/Q_d)/\delta Q_d = 1/A_{d,in} * \delta(A_{d,out}(Q_d))/\delta Q_d$$

In the equation above it is provided that the property of the dialysate before the dialyzer is not depending on the dialysate flow $Q_d$. If the property of the dialysate is for example the electrical conductivity, a before the dialyzer constant value of the electrical conductivity of the dialysate can be maintained for example due to an according modification of the amount of electrolytes injected into the dialysate. This is important in particular for the case in which the property of the dialysate is varied continuously in order to determine the change of the value of the control factor, as shown below.

Furthermore, in the equation for the derivation of the control factor $k_d/Q_d$ over the dialysate flow $Q_d$ the term $A_{d,out}(0)$ may be left out, which simplifies a determination of the derivation.

During a blood treatment the dialysate flow is varied and the change of the control factor $k_d/Q_d$ is determined. Thereby the variation of the dialysate flow can originate from a targeted modification of the dialysate flow or from changing parameters during the blood treatment. The determination of the change of the control factor $k_d/Q_d$ can take place within a targeted change of the dialysate flow by a determination of the control factor $k_d/Q_d$, each before and after the change of the dialysate flow or by a continuous determination of the derivation of the control factor $k_d/Q_d$ over the dialysate flow $Q_d$.

Then the change of the control factor determined in advance is compared with a limit value or a limit range with an upper value and a lower value. If the change of the control factor falls short of the limit value or the lower value of the limit, the dialysate flow is reduced. On the other hand, the dialysate flow is increased, if the change of the control factor exceeds the limit value or the upper value of the limit. For the limit value a value between 10 and 20 percent of the value of the control factor per change of the dialysate flow of 100 ml/min proved to be significantly advantageous. For each of these limit values a corresponding limit can be defined as well, which upper and lower limit specify a range of tolerance around the limit value. Thereby, the range of tolerance preferably comes to one percent of the value of the control factor per change of the dialysate flow of 100 ml/min, so that in terms of a limit value of 20 percent of the value of the control factor per change of the dialysate flow of 100 ml/min the lower and upper value of the limit range correspond to a value of 19.5 or 20.5 percent of the value of the control factor per change of the dialysate flow of 100 ml/min. Due to this control the dialysate flow is optimized according to the effectiveness of the dialyzer as well as to the consumption of dialysate and energy.

For a certain dialysate flow an associated ratio is arrived at for a property of the blood of a patient, as for example the electrical conductivity, temperature or the concentration of a marker substance such as Na ions, urea, uric acid, beta-2-microglobulin, wherein the ratio is of the value of the corresponding property of the dialysate after the dialyzer, i.e. when exiting the dialyzer, to the value of the corresponding property of the dialysate before the dialyzer, i.e. when entering the dialyzer. A change of the dialysate flow causes a change of the value of the corresponding property of the dialysate at the exit of the dialyzer. Thus, a determination of the change of the control factor based on a targeted change of the dialysate flow can be maintained by determining the control factor before and after the targeted change of the dialysate flow. Hereto, the value of the corresponding property of the dialysate is to be determined at a time after exiting the dialyser. Hereafter, it also has to be determined, when the targeted change of the dialysate flow has arrived at the outlet of the dialyzer, i.e. the hydraulic delay of the dialyzer for the particular dialysate flow has to be known, in order to be able to assign a change of the control factor to a certain change of the dialysate flow. The prior art states methods for determining the hydraulic delay of a dialyzer. The targeted change of the dialysate flow can be of a temporary, i.e. only lasting for a short time sequence, periodic or pulse-like change of the flow rate of the dialysate.

As an alternative to the targeted change of the dialysate flow in order to determine the change of the control factor, also the property of the dialysate before entering the dialyzer can be varied continuously, e.g. periodically. A continuous modulation of the value of the property of the dialysate when entering the dialyzer $A_{d,in}$ leads to a modulation of the value of the property of the dialyzer at the outlet of the dialyzer $A_{d,out}$. Accordingly, in a steady state, it is known what the value of the property of the dialysate should be at the outlet of the dialyzer at a certain time, so that a change of the dialysate flow can quickly be assigned to a change of the value of the property of the dialysate at the outlet of the dialyzer. Moreover, thus, the knowledge of the complex transfer function, as being dependent from the dialyzer-dialysance, modulation frequence and tube geometry, is not required.

For the case that the property of the dialysate is the electrical conductivity or the temperature of the dialysate, the illustration according to FIG. 1 for a dialysis treatment in the laboratory (in vitro) shows the chronological sequence of the electrical conductivity (left vertical axis) or the temperature (right vertical axis) of the dialysate before (graph C1) and after (graph C2) the dialyzer at a dialysate flow of 800 ml/min. Thereby, the almost harmonious variation of the electrical conductivity or the temperature of the dialysate when entering the dialyzer was generated by a volume dependent variation of the concentrate injection, i.e. the injection of electrolytes into the dialysate, or by the variation of the heating of the dialysate. The changes of the concentrations of the electrolytes or of the concentrations of a single electrolyte in a dialysate or the thermal modulation of the dialysate take place within the physiological harmless borders for a patient.

Due to the size of the dialyzer volume there is a mixture of volumes of different concentrations inside of the dialyzer, i.e. volumes with different values of the property of the dialysate. This mixture leads to a damping of the modulation, i.e. of the variation of the electrical conductivity or of the temperature of the dialysate escaping from the dialyzer, so that the amplitude of the electrical conductivity or the temperature of the dialysate escaping from the dialyzer is reduced depending on the modulation period and the dialyzer volume. Furthermore, a part of the modulated volume gets through the semi-permeable membrane into the extracorporeal cycle (blood stream), whereby the modulation of the electrical conductivity or the temperature of the dialysate escaping from the dialyzer is reduced additionally. The damping of the modulation can be recognized clearly in the illustration according to FIG. 1 by a comparison of curves C1 and C2, in particular by a comparison of the amplitudes.

The values of the electrical conductivity or the temperature of the dialysate before and after the dialyzer can be detected by means of measuring cells. From the data of the measuring cells the effect of a change of the dialysate flow can be detected directly, so that a control and thus optimization of the dialysate flow can be carried our very quickly.

Figure 2:
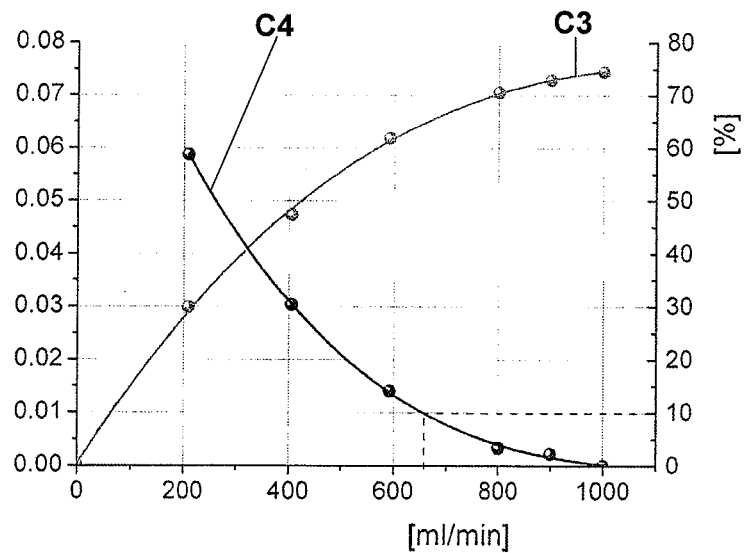

In the illustration according to FIG. 2, the amplitude ratio of the values of the electrical conductivity or the temperature of the dialysate before and after the dialyzer are represented as function of the dialysate flow (curve C3 with left vertical axis) and the relative change of the amplitude ratio is represented as a function of the dialysate flow (curve C4 with right vertical axis).

The curve C3 shows that the increase and thus the change of the amplitude ratio of the values of the electrical conductivity or the temperature of the dialysate before and after the dialyzer decreases more and more with the increase of the dialysate flow. Accordingly, curve C4 shows that the relative change of the amplitude ratio decreases with the increase of the dialysate flow. Already from a value of the dialysate flow of around 650 ml/min the relative change of the amplitude ratio and thus the increase of the effectiveness of the dialyzer is only less than 10 percent.

As an alternative to the determination of a change of the control factor by a detection of the value of the property of the dialysate at the exit of the dialyzer and of the value of the property of the dialysate before entering into the dialyzer, i.e. by a detection of a change of the property of the dialysate on the side of the dialysate, a property transferred in the dialyzer from the dialysate to the blood can also be measured on the blood side, i.e. by detection of the according property of the blood at the exit of the dialyzer and before entering into the dialyzer. For example, the transfer of a temperature bolus in the dialysate over the dialyzer onto the blood can be measured inside a venous tubing system. The control factor that also contains the effected mass of the treatment as function of the dialysate flow reads in this case $$k_b = Q_b * (A_{b,out}(Q_d) - A_{b,out}(0))/A_{b,in}$$

Therein $Q_b$ describes the blood flow, i.e. the flow rate of the blood, and $Q_d$ describes the dialysate flow in the dialyzer. $A_{b,in}$ describes a property of the blood as for example the electrical conductivity or the temperature of the blood before entering into the dialyzer and $A_{b,out}$ describes the respective property of the blood at the exit of the dialyzer. $A_{b,out}(0)$ gives the value of the property of the blood at the exit of the dialyzer at missing cleaning performance.

Here, again, it is advantageous not to use the control factor $k_b$ directly, but to use the derivation of the control factor $k_b$, divided by the blood flow $Q_b$, over the dialysate flow $Q_d$, hence, the change of the control factor $k_b/Q_b$ due to the change of the dialysate flow $Q_d$.

Thus, the invention also allows a control of the dialysate flow by means of a variation of a property of the dialysate and detection of a change of the according property of the blood on the side of the blood.

Also in case of a determination of the change of the control factor due to a targeted change of the dialysate flow the detection required for this of a change of a property of the dialysate or of the blood can be carried out on the side of the dialysate or on the side of the blood.

In order to determine a change of the control factor alternatively to the variation of a property of the dialysate before entering the dialyzer, a property of the blood before entering into the dialyzer can also be varied continuously, for example periodically, and the effect of the treatment on the property of the blood at the exit of the dialyzer can be measured on the side of the blood or alternatively on the side of the dialysate. So the variation of a property of the blood before entering into the dialyzer can consist of a small, patient compatible variation of the temperature of the blood. The variation of the heparin input into the blood before entering into the dialyzer is also possible. In case of a haemodialysis heparin or an alternative anticoagulation drug (citrate) is added continuously to the blood of the patient before entering into the dialyzer, in order to prevent clotting of the dialyzer. This occurs for example with a syringe pump that contains the according drug. The flow rate of this pump (heparin pump) can be modulated accordingly. As a further alternative the substitution rate can also be modulated. For the pre-dilution preferred to the applied hereby a sterile substitute is added to the blood of the patient before entering into the dialyzer. The excess water is withdrawn again from the blood of the patient by ultra-filtration over the dialyzer. The ingredients of the substitute in the blood as, for example, glucose, sodium, potassium, magnesium, calcium and bicarbonate pass-over within the dialyzer from the blood side to the dialysate side and are at least indirectly detectable there, for example the electrolytes by means of conductivity measurement cells.

Thus, the invention also allows a control of a dialysate flow by means of a variation of a property of the blood and detection of a change of the property of the blood on the blood side or on the dialysate side.

The easiest method for the determination of the amplitude ratio of the values of the electrical conductivity of the dialysate before ($LF_{d,in}$) and after the dialyzer ($LF_{d,out}$) is to compare the amplitude values or peak-to-peak-values of the electrical conductivity of the dialysate when entering into the dialyzer ($LF_{d,in}$) and at the exit of the dialyzer ($LF_{d,out}$) with each other. However, this approach has the disadvantage that noise and/or disturbances directly lead to measurement errors, which in turn reduces the accuracy of the determined amplitude ratio. Hence, in the curve C2 of the illustration according to FIG. 1 the disturbances in the value of the electrical conductivity of the dialysate at the exit of the dialyzer are circa 10 percent. Thus, it is necessary to average over a corresponding number of half periods T/2 in order to increase the accuracy.

Hence, it is more favorable to work with an averaging of the signals by comparing the absolute values of the areas under the conductivity curves:

$$\frac{\int_0^{i \cdot T/2} |LF_{d,in}(t) - \overline{LF_{d,in}}| \cdot dt}{\int_0^{j \cdot T/2} |LF_{d,out}(t) - \overline{LF_{d,out}}| \cdot dt}$$

Thereby, all measurement values of the time t are considered, whereby the statistical error is maximally reduced. However, this requires the determination of the mean values of the electrical conductivity of the dialysate when entering into the dialyzer and at the exit of the dialyzer from retrograded half waves, which on the one hand extends the entire averaging period and on the other hand can lead to systematic measurement errors, as for example in the case of drifts. Another option would be to firstly store all measurement values and to carry out the calculation afterwards. This, however, requires a high storage capability.

Hence, it is favorable to work with the standard deviations of the signals or the effective values of the alternating components by comparing the variances of the curves of the electrical conductivity of the dialysate:

$$\frac{\int_0^{i \cdot T/2} (LF_{d,in}(t) - \overline{LF_{d,in}})^2 \cdot dt}{\int_0^{j \cdot T/2} (LF_{d,out}(t) - \overline{LF_{d,out}})^2 \cdot dt} =$$

$$\frac{\int_0^{i \cdot T/2} (LF_{d,in}(t))^2 \cdot dt - \frac{1}{i \cdot T/2} \cdot \left(\int_0^{i \cdot T/2} LF_{d,in}(t) \cdot dt\right)^2}{\int_0^{j \cdot T/2} (LF_{d,out}(t))^2 \cdot dt - \frac{1}{j \cdot T/2} \cdot \left(\int_0^{j \cdot T/2} LF_{d,out}(t) \cdot dt\right)^2}$$

Hereby, in practice only the values $LF_{d,in}/LF_{d,out}$ and $LF^2_{d,in}/LF^2_{d,out}$ have to be summed-up over complete half waves.

The methods described above for determining the amplitude ratio of the values of the electrical conductivity of the dialysate before and after the dialyzer can be applied to values of other properties of the dialysate or the blood in an analogous manner.

The dialysate flow can be generated and changed by means as for example pumps and/or valves.

For the determination of the control factor from the values of the property of the dialysate or the blood before and after the dialyzer as well as for the determination of the derivation of the control factor from the dialysate flow, programmable microprocessors can be used for instance, which can also be used within a control unit for the control of the dialysate flow and the associated generation of commands for pumps and/or valves. The control facility preferably contains a storage for storing the requirements for the limit value or the limit range and for a program that can carry out the method according to the invention. Additionally, it can also be provided that the requirements for the limit value or the limit range at the start or during the execution of the program can be changed, so that instead of a default value of for example 20 percent of the value of the control factor per change of the dialysate flow of 100 ml/min also a value of for example 5 percent of the value of the control factor per change of the dialysate flow of 100 ml/min can be adjusted. It can also be provided that the range of tolerance of a limit, i.e. the upper limit and/or the lower bound of the limit can be changed at the start or during the execution of the program.

It can be concluded that due to the invention the dialysate flow in a dialysate device with regard to the effectiveness of the dialyzer and, thus, also the blood treatment is optimized independently from the knowledge of the used dialyzer type, the blood flow or certain patient parameters. An exceeding increase of the dialysate flow does not lead to a significant increase of the effectiveness of the dialyzer.

The invention claimed is:

1. A method for controlling a dialysate flow, the method comprising the steps of:
perfusing a blood chamber of a dialyzer with blood and a dialysis chamber, which is separated from the blood chamber by a semi-permeable membrane, with a dialysate,
controlling the dialysate flow through the dialysis chamber of the dialyzer when the value of a control factor is changed and does not lie within a limit range, caused by a continuous modulation of a property of the dialysate, whereby the control factor is a measure for the exchange of substances via the dialyzer and the controlling includes:

continuously modulating the value of the property of the dialysate, determining the change of the value of the control factor caused by continuously modulating the property of the dialysate during treatment, and increasing the dialysate flow if the change of the value of the control factor exceeds the limit range, or reducing the dialysate flow if the change of the value of the control factor falls below the limit range.

2. The method according to claim 1, wherein for determining the change of the value of the control factor, the property of the dialysate is continuously modulated for at least a time interval.

3. The method according to claim 1, wherein the property of the dialysate is the electrolyte concentration or the temperature.

4. A device for controlling a dialysate flow, comprising a dialyzer with a blood chamber for perfusing with blood and a dialysis chamber separated from the blood chamber by a semi-permeable membrane for perfusing with a dialysate, a generator for perfusing the dialysate flow through the dialysis chamber, a determining unit configured for determining a change in the value of a control factor that is a measure for the exchange of substances over the dialyzer, based on a modulation in the values of a property of the dialysate determined before and after the dialyzer, respectively, and a control facility configured to control the dialysate flow through the dialysis chamber of the dialyzer, if a property of the dialysate is modulated during treatment and if a change of the value of the control factor continuously at any time point during treatment caused by the modulation of a property of the dialysate does not lie within a limit range, the control facility instructs the generator to increase the dialysate flow if the change of the value of the control factor exceeds the limit range, and to reduce the dialysate flow, if the change of the value of the control factor falls below the limit range.

5. The device according to claim 4, wherein the device further has means for continuously modulating the property of the dialysate.

6. The device according to claim 4, wherein the property of the dialysate is the electrolyte concentration or the temperature.

7. A device for the extra-corporeal blood treatment comprising a device according to claim 4.

8. The method according to claim 1, further comprising adding a substitute to the blood before the perfusing step.

* * * * *